US009439567B2

(12) United States Patent
Carter et al.

(10) Patent No.: US 9,439,567 B2
(45) Date of Patent: Sep. 13, 2016

(54) UPDATING FIRMWARE TO CUSTOMIZE THE PERFORMANCE OF A WEARABLE SENSOR DEVICE FOR A PARTICULAR USE

(71) Applicants: Abraham Carter, Salt Lake City, UT (US); David Scott, North Salt Lake City, UT (US)

(72) Inventors: Abraham Carter, Salt Lake City, UT (US); David Scott, North Salt Lake City, UT (US)

( * ) Notice: Subject to any disclaimer, the term of this patent is extended or adjusted under 35 U.S.C. 154(b) by 175 days.

(21) Appl. No.: 13/891,699

(22) Filed: May 10, 2013

(65) Prior Publication Data

US 2014/0223421 A1  Aug. 7, 2014

Related U.S. Application Data

(60) Provisional application No. 61/761,635, filed on Feb. 6, 2013.

(51) Int. Cl.
| | |
|---|---|
| *G06F 9/44* | (2006.01) |
| *G06F 9/445* | (2006.01) |
| *A61B 5/00* | (2006.01) |
| *A61B 5/11* | (2006.01) |
| *A61B 5/145* | (2006.01) |
| *A61B 5/1455* | (2006.01) |
| *A61B 5/0205* | (2006.01) |

(52) U.S. Cl.
CPC ........... *A61B 5/0022* (2013.01); *A61B 5/0024* (2013.01); *A61B 5/1118* (2013.01); *A61B 5/14532* (2013.01); *A61B 5/14551* (2013.01); *G06F 8/65* (2013.01); *A61B 5/02055* (2013.01); *A61B 5/1123* (2013.01)

(58) Field of Classification Search
CPC .. G06F 8/65; G06F 8/71; A61B 5/01–5/026; A61B 5/0022; A61B 5/0024; A61B 5/1118; A61B 5/14532; A61B 5/4551; A61B 5/1123; A61B 5/02055

See application file for complete search history.

(56) References Cited

U.S. PATENT DOCUMENTS

| | | | |
|---|---|---|---|
| 2002/0165462 A1* | 11/2002 | Westbrook ........... | A61B 5/0205 600/529 |
| 2004/0107065 A1* | 6/2004 | Al-Ali ................ | A61B 5/14551 702/104 |
| 2007/0250830 A1 | 10/2007 | Holmberg et al. | |
| 2008/0005733 A1 | 1/2008 | Ramachandran et al. | |
| 2008/0139910 A1* | 6/2008 | Mastrototaro et al. ....... | 600/365 |
| 2008/0207232 A1* | 8/2008 | Rice et al. .................... | 455/466 |
| 2008/0208016 A1 | 8/2008 | Hughes et al. | |
| 2008/0301665 A1* | 12/2008 | Charlton et al. .............. | 717/170 |

(Continued)

OTHER PUBLICATIONS

Uwe Maurer, Location and Activity Recognition Using eWatch: A Wearable Sensor Platform, 2006, pp. 1-17.*

(Continued)

*Primary Examiner* — Thuy Dao
*Assistant Examiner* — Mongbao Nguyen
(74) *Attorney, Agent, or Firm* — Michael F. Krieger; Kirton McConkie

(57) ABSTRACT

The present invention is directed to providing customized versions of firmware to a wearable sensor device. The customized versions of the firmware can allow one or more sensors in the wearable sensor device to perform in a manner that is most optimal for a particular user or the particular manner in which the wearable sensor device is used. In some cases, the customizations can include causing the sensors to use a sampling rate that is optimal for one or more activities that the particular user intends to perform while wearing the wearable sensor device.

17 Claims, 10 Drawing Sheets

(56) References Cited

U.S. PATENT DOCUMENTS

| | | | |
|---|---|---|---|
| 2009/0088820 A1* | 4/2009 | Mao | A61N 1/37264 607/59 |
| 2009/0326417 A1* | 12/2009 | Ales, III | A61F 13/84 600/584 |
| 2010/0292600 A1* | 11/2010 | DiBenedetto | A63B 24/0062 600/520 |
| 2011/0021273 A1* | 1/2011 | Buckley et al. | 463/31 |
| 2011/0161100 A1* | 6/2011 | Peak et al. | 705/2 |
| 2011/0188684 A1 | 8/2011 | Spieler et al. | |
| 2011/0273287 A1* | 11/2011 | LaLonde et al. | 340/539.12 |
| 2011/0289497 A1* | 11/2011 | Kiaie | G06F 8/65 717/171 |
| 2012/0083705 A1* | 4/2012 | Yuen | A61B 5/0002 600/508 |
| 2012/0096451 A1* | 4/2012 | Tenbarge et al. | 717/170 |
| 2012/0226117 A1* | 9/2012 | Lamego | A61B 5/14532 600/316 |
| 2012/0316406 A1* | 12/2012 | Rahman et al. | 600/301 |
| 2012/0317167 A1* | 12/2012 | Rahman | G06Q 50/22 709/202 |
| 2012/0317430 A1* | 12/2012 | Rahman | G06F 1/3296 713/323 |
| 2012/0330109 A1* | 12/2012 | Tran | A61N 5/4076 600/301 |
| 2013/0074061 A1* | 3/2013 | Averbuch et al. | 717/171 |
| 2013/0104120 A1* | 4/2013 | Arrizza | G06F 8/65 717/173 |
| 2013/0177188 A1* | 7/2013 | Apfel | H04R 25/558 381/315 |
| 2013/0198694 A1* | 8/2013 | Rahman | G06F 3/0484 715/864 |
| 2013/0198730 A1* | 8/2013 | Munireddy et al. | 717/170 |
| 2013/0237861 A1* | 9/2013 | Margarida | A61B 5/0006 600/483 |
| 2013/0253600 A1* | 9/2013 | Drew et al. | 607/5 |
| 2013/0283256 A1* | 10/2013 | Proud | H01F 38/14 717/172 |
| 2014/0028456 A1* | 1/2014 | Sadhu | 340/539.13 |
| 2014/0053144 A1* | 2/2014 | Jose | G06F 8/65 717/168 |
| 2014/0055589 A1* | 2/2014 | Bangera | G06F 19/3418 348/77 |
| 2014/0247140 A1* | 9/2014 | Proud | A61B 5/02055 340/870.02 |
| 2014/0250430 A1* | 9/2014 | Proud | H01F 38/14 717/168 |

OTHER PUBLICATIONS

Richard Ribon Fletcher, iCalm: Wearable Sensor and Network Architecture for Wirelessly Comminicating and Logging Autonomic Activity, 2010, pp. 216-222.*

Camille Jaggernauth, Test Firmware Architecture for a Flexible Wireless Physiological Multi-Sensor, 2011, pp. 1-5.*

* cited by examiner

UPDATING FIRMWARE TO CUSTOMIZE THE PERFORMANCE OF A WEARABLE SENSOR DEVICE FOR A PARTICULAR USE

CROSS-REFERENCE TO RELATED APPLICATIONS

This application claims priority to U.S. Provisional Patent Application No. 61/761,635, titled Identifying Physiological Parameters From Raw Data Received Wirelessly From A Sensor, which was filed Feb. 6, 2013.

BACKGROUND

Many devices have been developed for tracking a user's performance during exercise. For example, GPS watches can track the distance traveled by a user wearing the watch, pedometers can track the number of steps a user takes, and other sensors can be used to measure one or more physiological parameters of the user during exercise such as a heart rate. Such devices include hardware for performing the desired measurements and firmware for controlling the hardware in the appropriate manner.

With such devices, it is common to provide periodic updates to the firmware to improve the functionality of the devices in some manner. For example, firmware updates often fix an error device's firmware that was not initially known but was manifest during use of the device. Firmware updates can also take advantage of hardware capabilities that were previously unused by prior versions of the firmware.

In such cases, the firmware initially provided with the hardware and any updates to the firmware are generic in the sense that they are not custom tailored to any particular device. For example, firmware or a firmware update may be specific to a group of devices (e.g. a specific model of a phone), but is not customized based on a characteristic unique to a particular device. Because of this, when a firmware update is created, the update is generally released to the general public so that anyone with the intended device can download the update to the intended device. In this way, all updated devices receive the same version of the firmware update.

BRIEF SUMMARY

The present invention extends to methods, systems, and computer program products for providing a customized version of firmware for controlling the functionality of a wearable sensor device. The customized version of the firmware can be customized based on how a particular wearable sensor device is used or one or more characteristics of a user that intends to use or has used the wearable sensor device. In this way, the functionality provided by the wearable sensor device can be tailored to a particular way in which the user uses the wearable sensor device.

In one embodiment, the present invention is implemented as a method for providing a firmware update to a wearable sensor device where the firmware update is customized for a particular user that uses the wearable sensor device. A mobile device receives information about a particular user that uses a wearable sensor device that includes one or more sensors for generating sensor data during one or more activities performed by the particular user. It is determined from the information about the particular user that a first version of firmware installed on the wearable sensor device for controlling at least one of the one or more sensors is not optimal. A second version of the firmware is generated. The second version of the firmware is customized, based on the information about the particular user, to control the at least one of the one or more sensors in a more optimal manner. The mobile device then transmits the second version of the firmware to the wearable sensor device such that the second version of the firmware is installed on the wearable sensor device to control the at least one of the one or more sensors in the more optimal manner.

In some embodiments, the information used to determine how to customize the second version of the firmware includes one or more activities that a particular user intends to perform while wearing the wearable sensor device.

In some embodiments, the customization made by the second version of the firmware includes causing one or more sensors in the wearable sensor device to use a different sampling rate that is optimal for one or more activities intended to be performed by the particular user.

In some embodiments, the customization can be based on one or more characteristics or preferences of the particular user. These customizations can cause a sensor to perform more accurately or efficiently based on the characteristics or preferences of the user.

In some embodiments, additional customizations can be made to an application on the mobile device that receives sensor data to customize the user experience to the particular user.

This summary is provided to introduce a selection of concepts in a simplified form that are further described below in the Detailed Description. This Summary is not intended to identify key features or essential features of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Figure 1:
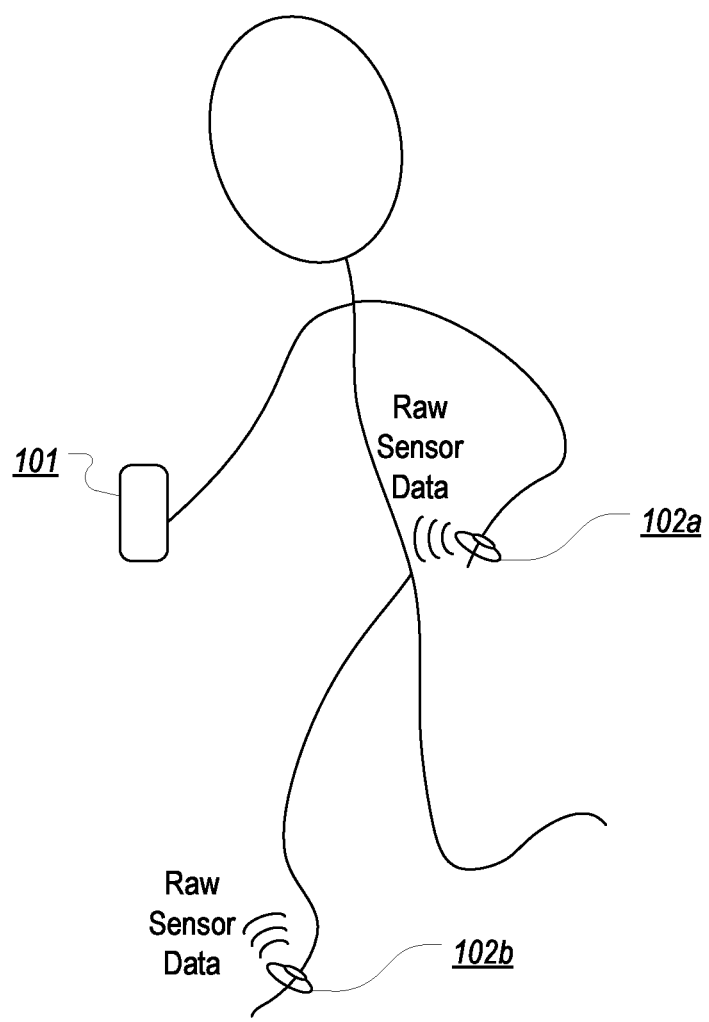
FIG. 1 illustrates an exemplary computing environment in which the present invention can be implemented.

The present invention extends to methods, systems, and computer program products for providing a customized version of firmware for controlling the functionality of a wearable sensor device. The customized version of the firmware can be customized based on how a particular wearable sensor device is used or one or more characteristics of a user that intends to use or has used the wearable sensor device. In this way, the functionality provided by the wearable sensor device can be tailored to a particular way in which the user uses the wearable sensor device.

In one embodiment, the present invention is implemented as a method for providing a firmware update to a wearable sensor device where the firmware update is customized for a particular user that uses the wearable sensor device. A mobile device receives information about a particular user that uses a wearable sensor device that includes one or more sensors for generating sensor data during one or more activities performed by the particular user. It is determined from the information about the particular user that a first version of firmware installed on the wearable sensor device for controlling at least one of the one or more sensors is not optimal. A second version of the firmware is generated. The second version of the firmware is customized, based on the information about the particular user, to control the at least one of the one or more sensors in a more optimal manner. The mobile device then transmits the second version of the firmware to the wearable sensor device such that the second version of the firmware is installed on the wearable sensor device to control the at least one of the one or more sensors in the more optimal manner.

In some embodiments, the information used to determine how to customize the second version of the firmware includes one or more activities that a particular user intends to perform while wearing the wearable sensor device.

In some embodiments, the customization made by the second version of the firmware includes causing one or more sensors in the wearable sensor device to use a different sampling rate that is optimal for one or more activities intended to be performed by the particular user.

In some embodiments, the customization can be based on one or more characteristics or preferences of the particular user. These customizations can cause a sensor to perform more accurately or efficiently based on the characteristics or preferences of the user.

In some embodiments, additional customizations can be made to an application on the mobile device that receives sensor data to customize the user experience to the particular user.

Example Computer Architecture

Embodiments of the present invention may comprise or utilize special purpose or general-purpose computers including computer hardware, such as, for example, one or more processors and system memory, as discussed in greater detail below. Embodiments within the scope of the present invention also include physical and other computer-readable media for carrying or storing computer-executable instructions and/or data structures. Such computer-readable media can be any available media that can be accessed by a general purpose or special purpose computer system.

Computer-readable media is categorized into two disjoint categories: computer storage media and transmission media. Computer storage media (devices) include RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other similarly storage medium which can be used to store desired program code means in the form of computer-executable instructions or data structures and which can be accessed by a general purpose or special purpose computer. Transmission media include signals and carrier waves.

Computer-executable instructions comprise, for example, instructions and data which, when executed by a processor, cause a general purpose computer, special purpose computer, or special purpose processing device to perform a certain function or group of functions. The computer executable instructions may be, for example, binaries, intermediate format instructions such as assembly language or P-Code, or even source code.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like.

The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices. An example of a distributed system environment is a cloud of networked servers or server resources. Accordingly, the present invention can be hosted in a cloud environment.

Example Computing Environment Including Mobile Device and Wearable Sensor

FIG. 1 illustrates an exemplary computer environment 100 in which the present invention can be implemented. Computer environment 100 includes a portable computing device 101 and sensors 102a, 102b that are worn by a user during a workout or other activity. In a typical implementation, portable computing device 101 can be a user's smart phone or other device capable of running a mobile application (e.g. an MP3 player or tablet). Sensors 102a, 102b can represent different types of sensors for detecting various physiological parameters. For example, in a particular embodiment, the sensors can include a blood glucose sensor, a pulse oximeter, a skin temperature sensor, or a blood pressure sensor. The term sensor should be understood as referring to either or both the individual sensor unit and the housing containing the sensor unit.

In some embodiments, in addition to the sensors for detecting various physiological parameters, one or more of the sensors can include an accelerometer that is used to detect specific movements of the user's body parts on which the sensors are worn. For example, in the particular embodiment shown in FIG. 1, sensor 102a is worn around the user's wrist (e.g. as a bracelet) and includes an accelerometer for determining the specific motion the user's arm makes during a workout. In such embodiments, sensor 102a can also include one or more sensors for detecting one or more of the user's physiological parameters during the workout.

Similarly, sensor 102b, as shown in FIG. 1, can be worn on or around the user's foot or ankle and provide accelerometer data representing the specific motion of the user's leg during the workout. Sensor 102b can also contain one or more sensors for detecting various physiological parameters.

Although FIG. 1 depicts two sensors 102a, 102b being worn around the wrist and on the foot respectively, the present invention is not limited to any specific number of sensors or any particular placement of the sensors on the user's body. For example, one or more sensors can be worn on the elbow, hip, knee, head, etc.

Figure 2A:
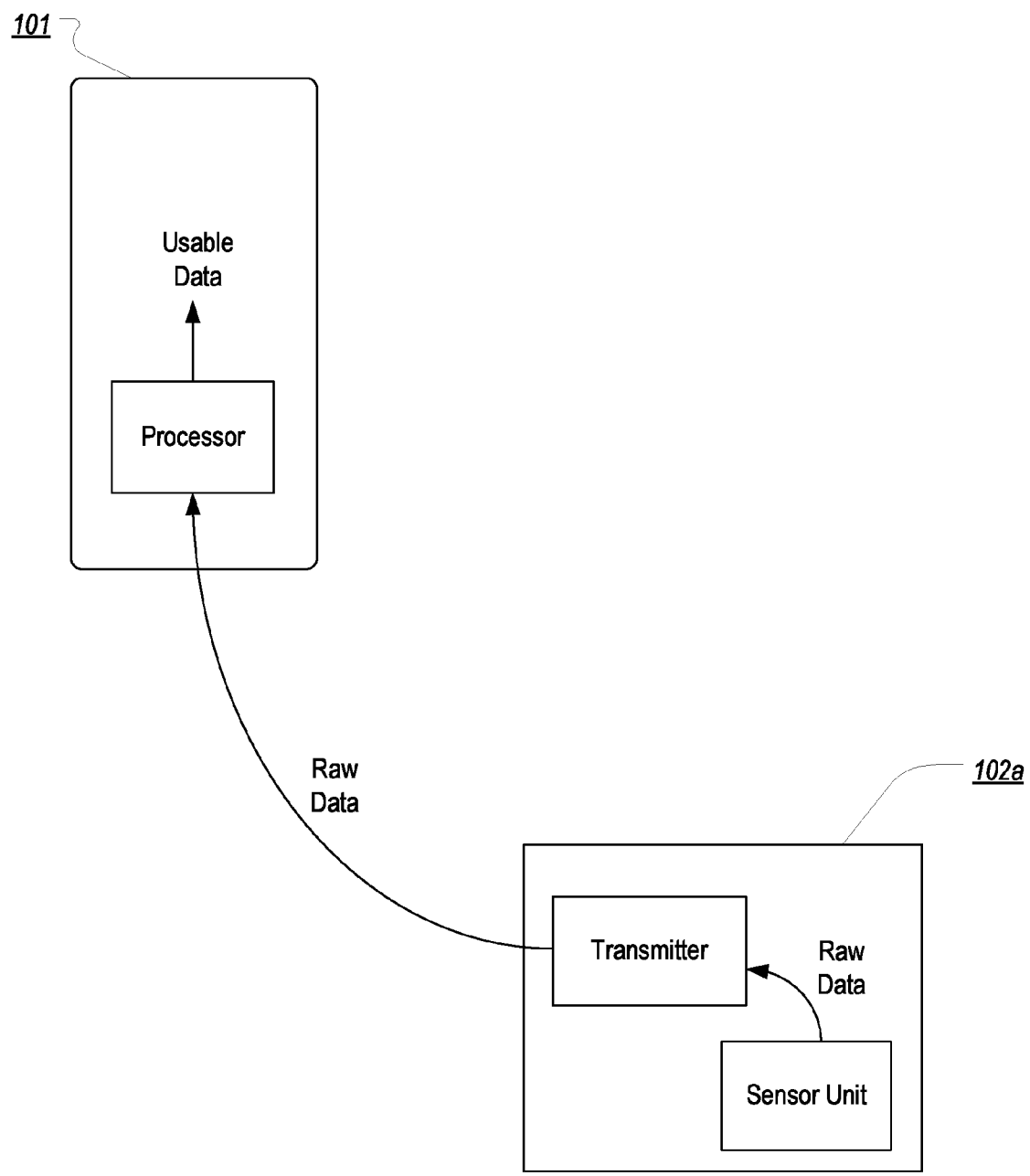
FIGS. 2A and 2B illustrate the transmission of raw sensor data between the sensors and the portable computing device of the present invention.
Figure 2B:
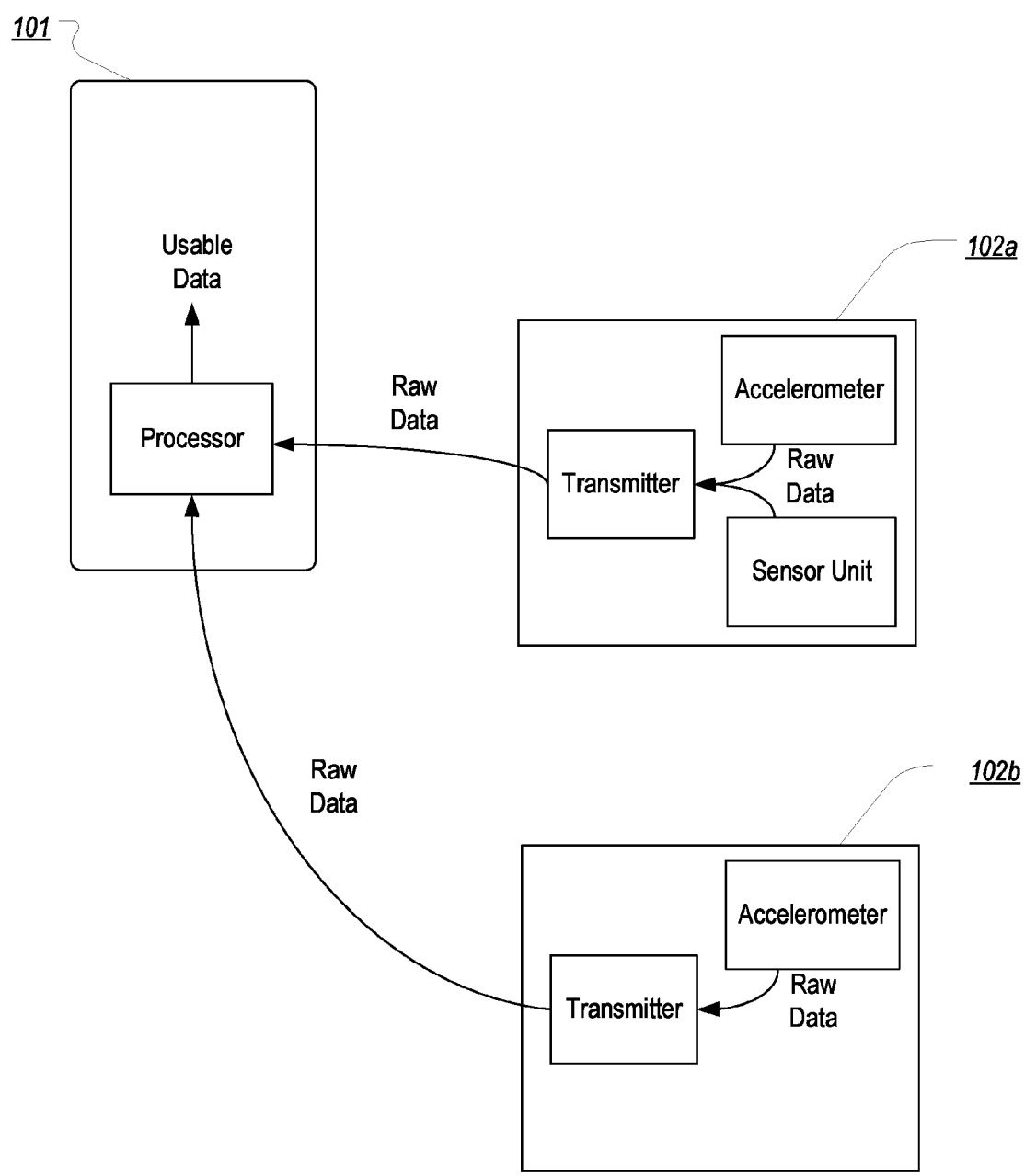

FIGS. 2A and 2B represent how a sensor can transmit raw data to portable computing device 101. Previous approaches process raw data received from a sensor into usable data prior to transmitting the usable data to another computing device. The present invention differs from this approach in that the sensor transmits raw data wirelessly to portable computing device 101. For example, using the techniques of the present invention, raw data from a pulse oximeter or a blood glucose monitor can be wirelessly transmitted directly to the user's smart phone where it is processed to generate usable data. In this way, the user does not need a specialized device, but can use his smart phone or other similar device to track physiological parameters. Because a user generally carries a smart phone or similar device at all times, processing raw data in this way (i.e. by transmitting the raw data directly to the smart phone for processing) allows for a simpler and more accessible system.

As shown in FIG. 2A, sensor 102a includes a sensor unit (e.g. a blood glucose monitor or pulse oximeter). Raw data output by the sensor unit is transmitted directly from sensor 102a to portable computing device 101 where it is processed into usable data. FIG. 2B illustrates that sensor 102a can also include an accelerometer whose raw data is also transmitted to portable computing device 101 where it is processed into usable data. FIG. 2B also shows that sensor 102b may only include an accelerometer. Of course, sensor 102b could also include one or more sensor units for generating raw data related to another physiological parameter which could be wirelessly transmitted to portable computing device 101 for processing.

In some embodiments, sensors 102a, 102b can be configured to intermittently transmit sensor data. This can be done to conserve battery power. For example, sensors 102a, 102b can include logic for determining when the sensor data is of particular importance, and transmit only the important data. In one example, sensors 102a, 102b can be configured to only transmit data when a significant change in the data has occurred. In such cases, portable computing device 101 can assume that the physiological parameter being sensed has not changed significantly until it again receives a transmission from the sensors.

Once portable computing device 101 has received and processed the raw data into usable data, the usable data can be displayed to the user carrying the portable computing device. For example, a mobile application on the user's smart phone can be used to view a measurement of the one or more physiological parameters.

In some embodiments, the raw data can also be transmitted to a server or other computing system where it can be further processed and analyzed. For example, the mobile application on portable computing device 101 can be configured to upload or otherwise transfer raw data to a central server system that stores raw data received from many different portable computing devices. This raw data can be compiled into a repository where further analysis can be performed to identify patterns, trends, tendencies, etc. which can later be provided to portable computing device 101 for automatic and immediate processing of raw data.

For example, if it is determined, after processing a large set of raw data from many different users, that a particular pattern appears in the raw data that can be used as an indicator that a user is performing to a maximum level or may be suffering from a condition, this pattern can be sent back to portable computing device 101. The portable computing device can then automatically scan new raw data being received from the sensors and notify the user if the pattern is detected in the new raw data. Examples of the types of conditions that can be identified in this manner include ideal training levels (e.g. $VO_2$ max, lactate threshold), over-training, depletion of blood glucose levels, etc.

Identifying that a particular pattern can serve as an indicator of some condition can be performed in any suitable way. Because portable computing device 101 receives the raw sensor data and will generally contain circuitry for transferring the raw data to a central server, the present invention facilitates this analysis. In other words, using the present invention, the raw sensor data (as opposed to processed and possibly proprietary data) can easily be provided to a central repository where it can more easily be processed.

This raw data can be mined to identify patterns or neural networks. Correlations can also be created between the raw data and activity data to enable the detection of the early onset of a disease or to enhance patient care monitoring.

FIG. 2B also represents a system that includes multiple accelerometer devices (or sensors) where at least one of the accelerometer devices also includes a sensor for detecting one or more physiological parameters. In this type of system, the user can wear the devices on various body parts (e.g. the wrist and foot). The accelerometers can route raw accelerometer data to portable computing device 101 (e.g. the user's smart phone) which processes the raw accelerometer data to determine specific movements the user is performing during a workout. For example, portable computing device 101 can detect, based on the raw accelerometer data, that the user is riding a bike, running, doing push-ups, pull-ups, curls, etc.

The additional raw data received from the one or more sensors for detecting physiological parameters can also be processed and correlated with the raw accelerometer data to provide additional feedback regarding how the specific movements or exercises are being performed (e.g. by matching time stamps so the appropriate sensor data is used with the accelerometer data generated at the same time as the sensor data). In other words, using this system, the user's portable computing device can track the specific type of exercise being performed (including the number of reps) while at the same time providing feedback regarding how well the user's body is responding by tracking physiological parameters. This tracking and monitoring can all be performed on portable computing device 101.

It is noted again that, although devices exist for detecting some physiological parameters including devices that can be worn during exercise, such devices are specialized for performing such detection and analysis. In contrast, the system of the present invention can employ a standard portable computing device that receives raw sensor data and processes the raw data to generate usable data.

In a specific example, the present invention would allow a user to use an app on his iPhone to track specific physiological parameters (rather than having to purchase a separate device (e.g. a watch or armband) that contains customized hardware/software for processing raw sensor data into a usable form). Accordingly, the present invention provides a simplified system for use during exercise or other activities. Because the sensors can transmit raw data directly to the portable computing device, and because the portable computing device can run a mobile application capable of processing the raw data, virtually anyone can begin tracking physiological parameters by simply wearing one or more sensors.

As another example of how the present invention improves on current systems, many users carry a phone or other audio device (e.g. an iPod) during exercise both as forms of entertainment (e.g. music) and for tracking distance traveled (e.g. via a GPS based application). For such a user to be able to monitor physiological parameters during a workout, the user must purchase a separate device (e.g. a watch or armband) that includes sensors for generating raw data and hardware/software for processing the raw data into a usable form and displaying the usable data. Such devices are expensive and require the user to carry multiple devices (assuming the user desires to also carry his phone).

In contrast, in the present invention, the user only needs to carry his phone because the sensors can transmit the raw data directly to the phone where an app processes the raw data and displays usable data on the phone's display. The phone also contains the necessary circuitry to upload or transfer the raw and/or usable data to another system for further use.

Providing Firmware Updates to a Wearable Sensor Device that are Customized for a Particular User of the Wearable Sensor In some embodiments, portable computing device 101 can be configured to communicate wirelessly with sensors 102a, 102b (e.g. via Bluetooth) to update firmware on the sensors. Updating the firmware in this manner enables the sensors to be customized for a particular user or a particular use of the sensors.

For example, a sensor may initially contain firmware (e.g. when sold) that causes the sensor to perform in a manner that would be most effective for an average person. However, because each individual user may use the sensor differently, the initial firmware may not provide the most optimized functionality for a particular user.

As an example, a wearable sensor device (which refers to the physical device worn by the user that may contain one or more sensors) that comprises an accelerometer may be sold with firmware that optimizes the functionality of the accelerometer when used for running. These optimizations, however, may cause the accelerometer to be less optimized when used for yoga. Because of this, a user that intends to use or has used the wearable sensor device to track yoga movements may not receive optimized movement tracking from the accelerometer. To address these types of scenarios, the present invention can identify how a particular user intends to use or has used a wearable sensor device, create a firmware update that is customized for the particular user's use of the wearable sensor device, and wirelessly transmit the customized firmware update to the wearable sensor device. In this way, each individual wearable sensor device can be customized for the particular user that is using or will use the wearable sensor device.

As another example, a wearable sensor device that comprises a pulse oximeter may be sold with firmware that optimizes the functionality of the pulse oximeter for a user having average skin density. However, if the user's skin has an increased density (and therefore requires a stronger intensity of light for the sensor to adequately work), the firmware can be adjusted so that a stronger light is emitted. Such determinations can be made during or after use of the pulse oximeter (e.g. by identifying that data received from the pulse oximeter is deficient), or prior to use (e.g. by receiving user input that indicates that a stronger light intensity may be desired).

Customizations to the firmware of a wearable sensor device can be based on many different factors. For example, prior to using a wearable sensor device, a user may complete a registration process during which the user provides information specifying the user's characteristics (e.g. height, weight, age, resting heart rate, etc.) and the intended uses of the wearable sensor device. Based on such information, a customized update to the firmware of the wearable sensor device can be created which tailors the functionality of the wearable sensor device to provide a more optimal experience for the user when wearing the wearable sensor device.

Similarly, after the user has begun using the wearable sensor device, he may provide additional information or modified information that can be used to identify customizations that can be made to the firmware. For example, if a user initially specified that he intended to use the wearable sensor device during running, but later decided to use the wearable sensor device during swimming, the user can provide such input to allow a firmware update to be created that is customized for the user's use of the wearable sensor device while swimming.

In addition to creating firmware updates in response to user input, a customized firmware update can also be created automatically by detecting that sensor data received from the wearable sensor device indicates that the wearable sensor device is not functioning in an optimal manner. For example, it can be determined that a particular sensor is taking readings too frequently or not frequently enough based on the particular way in which it is being used. In such cases, the firmware can be updated to decrease the sample rate (e.g. to conserve battery power), or to increase the sample rate (e.g. to more accurately identify a particular movement the user is performing).

The creation of a customized firmware update can be performed by the mobile device receiving data from the wearable sensor device or by another computing device in communication with the mobile device. For example, a mobile phone that the user carries (e.g. during exercise) can create the firmware update and wirelessly transmit the update to the wearable sensor device. Alternatively, a server can create the firmware update and transmit the update to the mobile device which then wirelessly transmits the update to the wearable sensor device. Further, in some embodiments, a computing device other than the mobile device receiving data from the wearable sensor device (e.g. a user's personal computer) can be used to receive a firmware update from a server and transmit the firmware update to the wearable sensor device. Accordingly, the present invention extends to providing a customized firmware update to a wearable sensor device using various types or number of devices.

In some embodiments, a firmware update can be made to customize how a wearable sensor device uses memory or a radio. For example, based on how the wearable sensor device is used or is intended to be used, it could be determined that the wearable sensor device will always be within range of the mobile device to which the wearable sensor device transmits sensor data. For example, a user may specify that he will always carry his mobile phone while wearing a wearable sensor device, or the mobile phone may determine that it is always in proximity of the wearable sensor device during use of the wearable sensor device. In such cases, there may never be a need for the wearable sensor device to store sensor date prior to transmitting the sensor data to the mobile device. Therefore, a customized firmware update can be generated and transmitted to the wearable sensor device that causes the wearable sensor device to continuously transmit sensor data to the mobile device without first storing the sensor data in memory. Examples where customizing the firmware so that sensor data is not stored in memory include when the user carries his phone while performing the exercise (e.g. while jogging, biking, hiking, golfing, etc.), when the user wears the wearable sensor device while exercising on a stationary device (e.g. a treadmill) with the mobile device nearby, when the user wears the wearable sensor device to monitor a movement or other parameter that is performed in a single location with the mobile device nearby (e.g. while sleeping, while lifting weights, while doing yoga, etc.).

Similarly, if the mobile device is never or rarely within range of the wearable sensor device during use (meaning that the sensor data must be stored until the mobile device is within range), a customized firmware update can be generated that causes the radio of the wearable sensor device to be turned off during use of the wearable sensor device. In this way, the wearable sensor device will not needlessly attempt to transmit data when the mobile device is not within range. In some cases, the radio can be customized to be turned off throughout the use of the wearable sensor device, or may be customized to make periodic scans to determine when the mobile device may be in range. Examples where customizing the firmware so that the radio is turned off during use include when the wearable sensor device is used during swimming (because the user probably will not carry his phone while swimming), or when the user does not desire to carry the mobile device while performing an exercise that requires traveling outside the range of the radio.

Figure 3A:
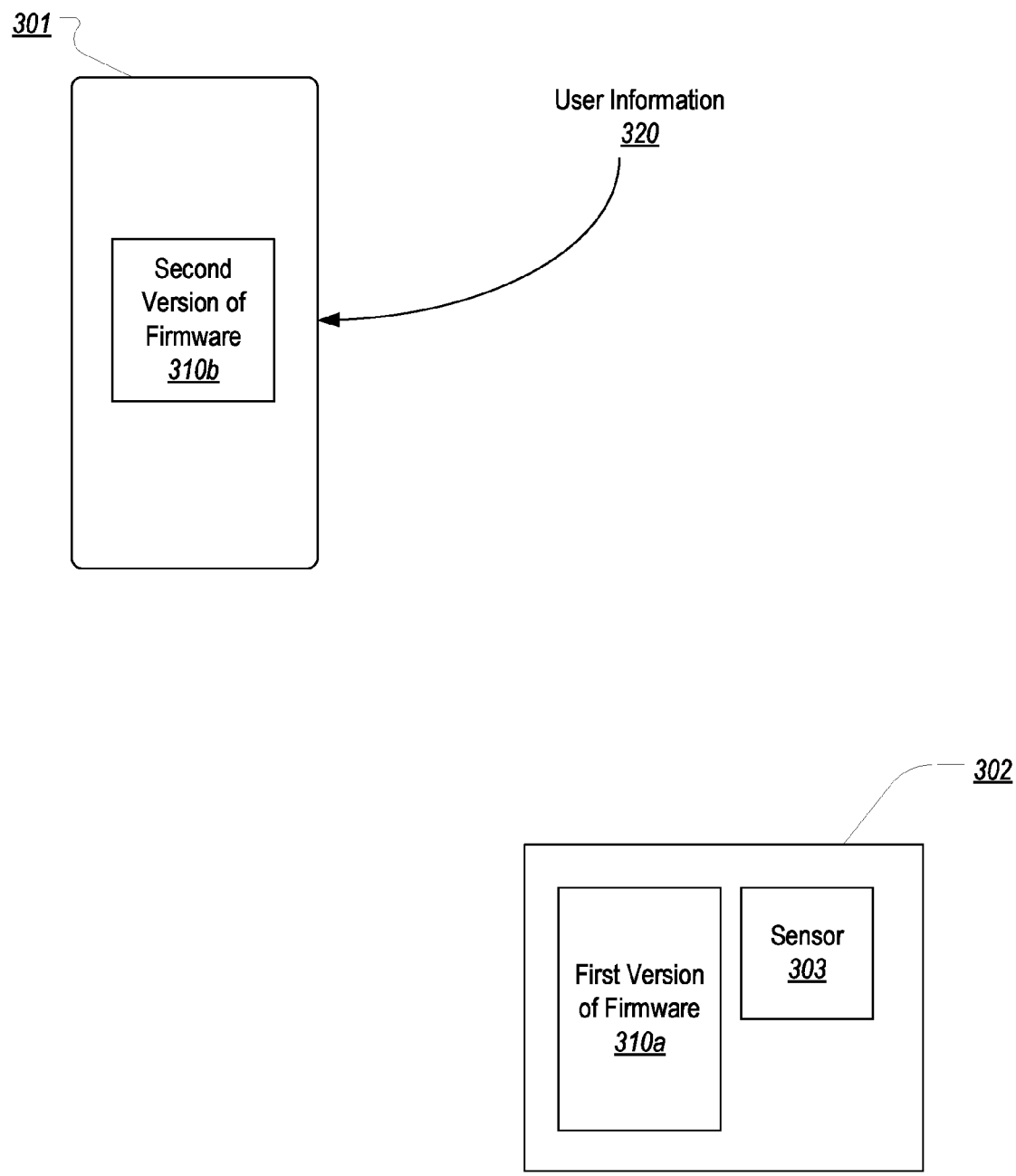
FIGS. 3A-3C illustrate a process of creating and installing a customized version of firmware on a wearable sensor device based on information obtained about a particular user.
Figure 3B:
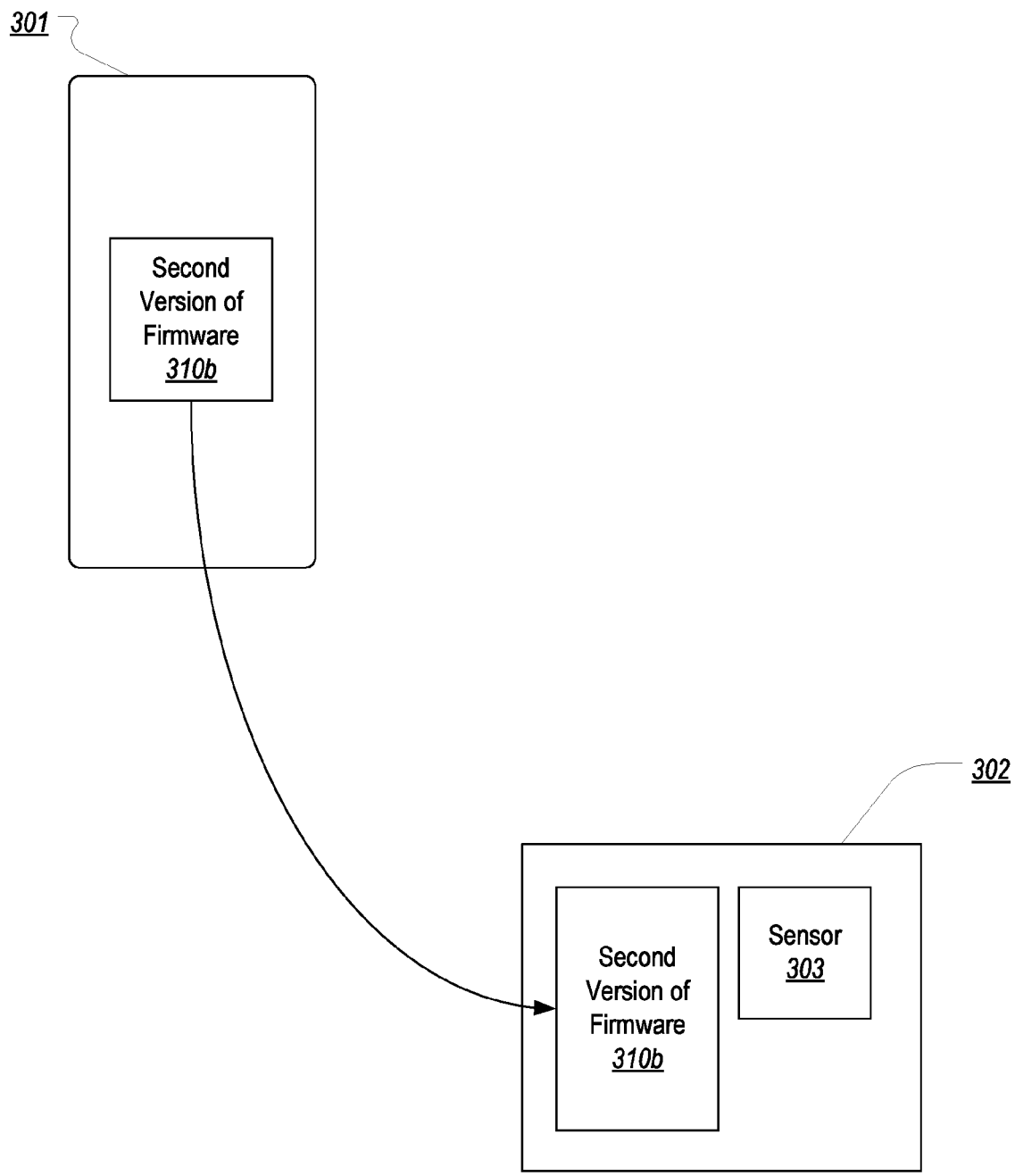
Figure 3C:
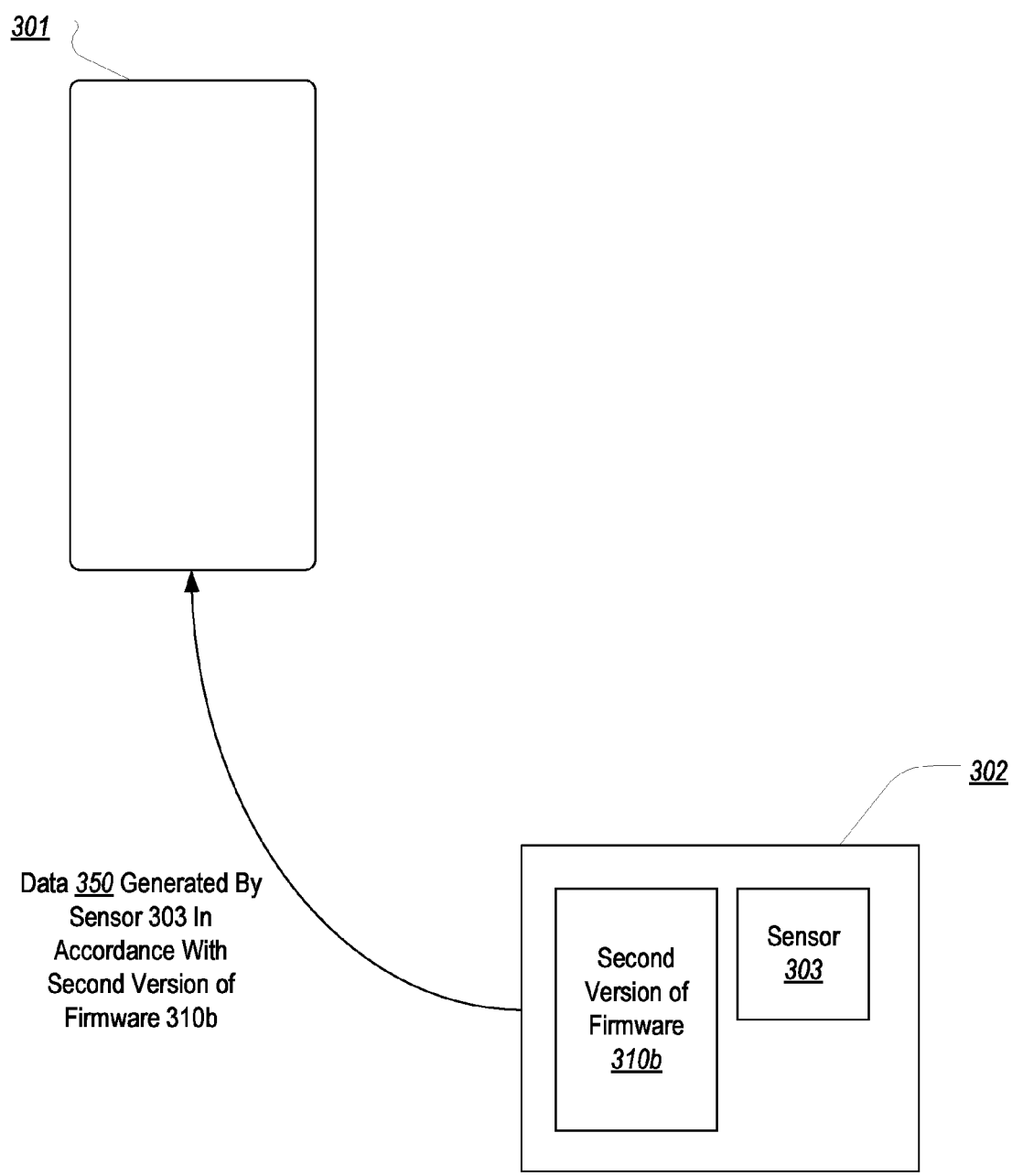

FIGS. 3A-3C illustrate an example of how a mobile device 301 can provide a customized firmware update to a wearable sensor device 302 that contains a sensor 303. This update to the firmware can occur in response to receiving information about the particular user that is or will be wearing wearable sensor device 302. Although wearable sensor device 302 is shown as having a single sensor 303, the process depicted in FIGS. 3A-3C can be used when a wearable sensor device includes more than one sensor. In other words, a customized firmware update can modify the functionality of one or more sensors in a wearable sensor device.

In FIG. 3A, wearable sensor device 302 is shown as having a first version of firmware 310a for controlling sensor 303. The first version 310a can be an initial version supplied with wearable sensor device 302 or an already updated version transmitted to wearable sensor device 302. FIG. 3A also shows that mobile device 301 receives user information 320. User information 320 can comprise any information about the user associated with wearable sensor device 302 including characteristics of the user, preferences of the user, the user's intended use of wearable sensor device 302, etc.

Based on user information 320, mobile device 301 can determine that the first version of firmware 310a which is currently installed on wearable sensor device 302 for controlling sensor 303 is not optimal. In response, mobile device 301 can generate a second version of firmware 310b which is customized for the user based on user information 320. These customizations can include modifying a sampling rate of sensor 303 or modifying another controllable parameter of sensor 303 (which will be different depending on the specific type of sensor).

In FIG. 3B, mobile device 301 is shown as wirelessly transmitting the second version of firmware 310b to wearable sensor device 302. Then, as shown in FIG. 3C, with the second version of firmware 310b being installed on wearable sensor device 302, sensor 303 generates data 350 in accordance with the second version of firmware 310b (e.g. using a customized sampling rate, a customized power level, a customized data set, etc.). Accordingly, data 350 generated after the second version of firmware 310b is installed can be optimized for the particular way in which the user is using or will be using wearable sensor device 302.

Figure 4A:
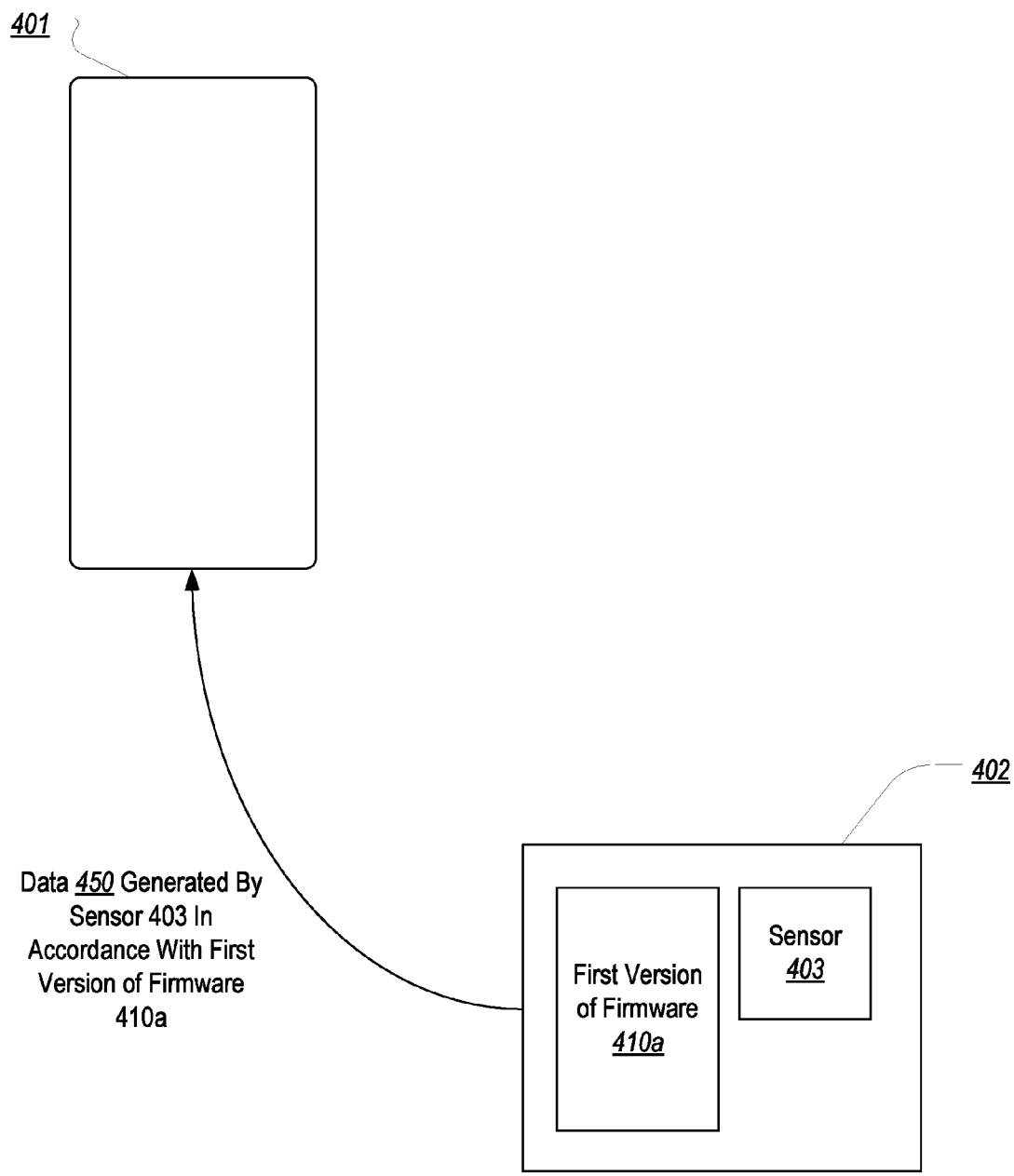
FIGS. 4A-4C illustrate a process of creating and installing a customized version of firmware on a wearable sensor device based on sensor data received from the wearable sensor device.
Figure 4B:
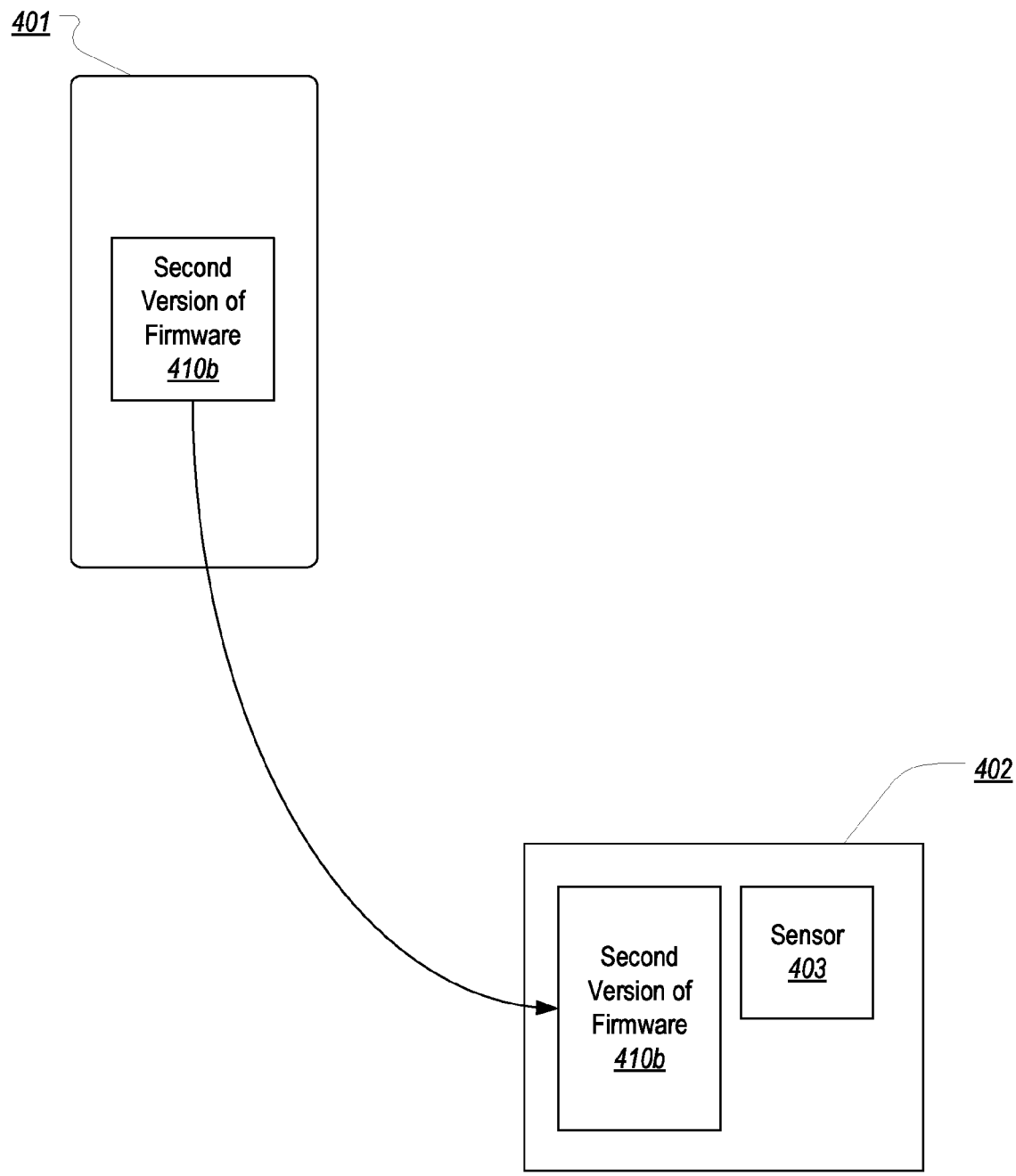
Figure 4C:
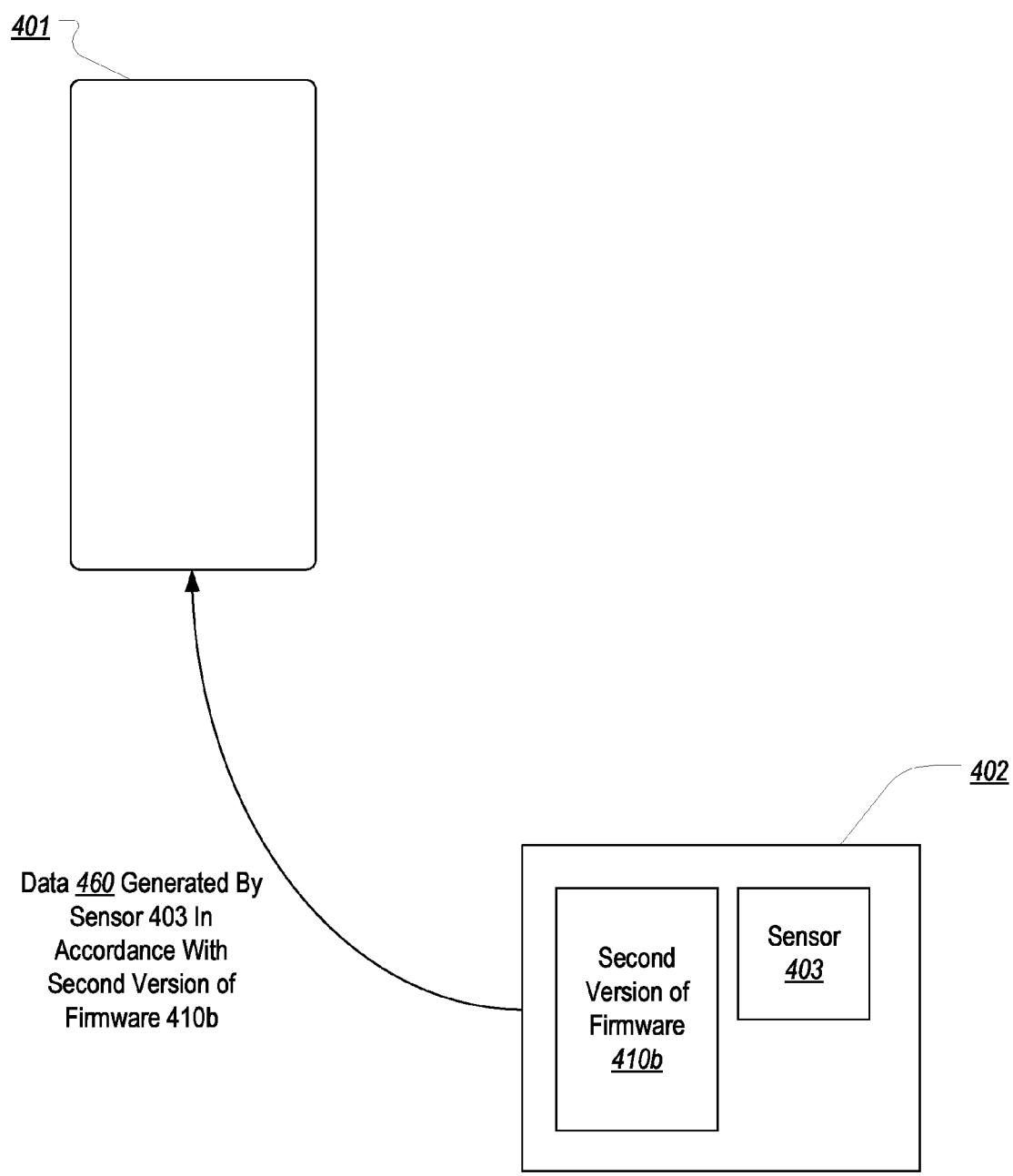

FIGS. 4A-4C illustrate another example of how a mobile device 401 can provide a customized firmware update to a wearable sensor device 402 that contains a sensor 403. This update to the firmware can occur in response to receiving sensor data and determining that the sensor data is not optimized for the particular way in which the user in using the wearable sensor. Although wearable sensor device 402 is shown as having a single sensor 403, the process depicted in FIGS. 4A-4C can be used when a wearable sensor device includes more than one sensor.

In FIG. 4A, wearable sensor device 402 is shown as having a first version of firmware 410a for controlling sensor 403. The first version 410a can be an initial version supplied with wearable sensor device 402 or an already updated version transmitted to wearable sensor device 402. FIG. 4A also shows that mobile device 401 receives data 450 generated by sensor 403 in accordance with the first version of firmware 410a. For example, data 450 can comprise accelerometer data (when sensor 403 is an accelerometer), hemoglobin saturation data (when sensor 403 is a pulse oximeter), blood glucose levels (when sensor 403 is a blood glucose monitor), or any other type of data generated by a sensor that can be incorporated into wearable sensor device 402 to provide meaningful data. It is also noted that data 450 can comprise a combination of data from multiple sensors. In other words, if wearable sensor device 402 includes multiple sensors, data 450 can include sensor data generated by any number of the multiple sensors.

Mobile device 401 (or another device with which mobile device 401 can communicate) can determine from data 450 that the first version of firmware 410a which is currently installed on wearable sensor device 402 for controlling sensor 403 is not optimal. In response, as shown in FIG. 4B, mobile device 401 (or another device) can generate a second version of firmware 410b which is customized for the particular way in which the user is using wearable sensor device 402 (as indicated by data 450). These customizations can include modifying a sampling rate of sensor 403 or modifying another controllable parameter of sensor 403 (which will be different depending on the specific type of sensor).

In FIG. 4B, mobile device 401 is shown as wirelessly transmitting the second version of firmware 410b to wearable sensor device 402 which replaces, updates, or otherwise modifies first version 410a. Then, as shown in FIG. 4C, with the second version of firmware 410b installed on wearable sensor device 402, sensor 403 generates data 460 in accordance with the second version of firmware 410b (e.g. using a customized sampling rate, a customized power level, a customized data set, etc.). Accordingly, data 460 generated after the second version of firmware 410b is installed can be optimized for the particular way in which the user is using wearable sensor device 402.

In each example shown in FIGS. 3A-3C and 4A-4C, the customized version of the firmware can be generated directly on the mobile device or may be generated on another computing device and then transferred to the mobile device. Accordingly, the particular location where the customized version of the firmware is generated is not essential to the invention. In any case, it is preferred that the user's mobile device transmit the customized version of the firmware to the wearable sensor device to provide the most user-friendly experience. For example, in some cases, this customization of the firmware can occur automatically without requiring user interaction even while the wearable sensor device is being used. In this way, the firmware can be updated dynamically so that each sensor of the wearable sensor device can provide the most optimal data for the particular user and for the way in which the particular user is using or intends to use the wearable sensor.

In some embodiments, in addition to customizing the firmware on the wearable sensor, the present invention can also include customizing an application running on the mobile device that receives sensor data from the wearable sensor device. For example, because a wearable sensor device can include sensors that may provide a substantial amount of data related to a large number of exercises or movements, an application executing on the user's mobile device needs the capability to process the large amount of sensor data it may receive. However, in most cases, a particular user will only use a wearable sensor device to monitor a subset of movements or parameters that the application is capable of identifying/tracking.

In such cases, the application on the user's mobile device can be customized based on how the user is using or intends to use the wearable sensor device. For example, if the user intends only to use the wearable sensor device to track the performance of pushups and the hemoglobin saturation level during the pushups, the application can be customized to process such data more efficiently. In this example, the application may be customized by deactivating the other movements that the application is configured to identify (e.g. running movements, biking movements, swimming movements, etc.) which may result in the application running more efficiently leading to quicker response times and reduced battery consumption.

Deactivating a movement can refer to causing the application to not compare sensor data of an unknown movement to the known data representing a particular activity. For example, if a database of known movements stores data representing the sensor data generated when each of one hundred different movements is performed, the application can be configured to only compare unknown sensor data generated by the wearable sensor device to the stored data representing the active movements. In this way, when the user performs a movement that is active, the application can potentially identify the movement using many fewer comparisons than when all movements are active because comparisons will not be made to the stored data representing deactivated movements.

Similarly, in some cases, the user may intend to use the wearable sensor device to identify a custom movement. In such cases, the application can be customized by creating and activating the custom movement while deactivating some or all of the other movements for which the application stores data. Similar customizations of the application can be made to optimize the type of data displayed to the user when a movement is identified.

In another example, customizations can be made to the application on the mobile device to generate custom tailored patterns for identifying particular movements in accelerometer data. For example, the application on the mobile device can include a database of known movements. These known movements can be represented as sequences of accelerometer data that are generated when the known movement is performed. Initially, the known movements in the database can be based on how a movement is typically or optimally performed. For example, the database can initially contain sequences generated when a professional athlete performs a repetition of an activity (i.e. the sequences may be initially modeled after a perfectly performed movement).

As the user uses the wearable sensor device and accelerometer data is generated while the user performs the movement, the application on the mobile device may identify that the sequences generated during the user's performance of the movement vary slightly from the sequences representing the known movement in the database. For example, the application can identify that the user is performing the movement, but can also identify that the user does not perform the movement in the same manner as a professional athlete from which the sequences of the known movement were modeled.

In response, the application can customize the stored sequences in the database representing the movement so that they more closely match how the user performs the movement. For example, if the user's jogging motion has more lateral movement than a professional athletes motion, the sequences stored in the database for the known jogging movement can be modified to more closely match a sequence that identifies the additional lateral movement.

Tailoring the known sequences stored in the database in this manner can enable the generation of more accurate results or estimates of various measurements. For example, if the user's jogging motion with the additional lateral movement burns more calories than a typical jogging motion, by customizing the stored sequences from which various measurements may be made (e.g. calories burned), the measurements can be more accurate for the particular user. In this way, the database of known movements can be custom tailored over time to more closely match the particular motions the user makes.

Accordingly, the user experience can be optimized by both customizing the firmware on the wearable sensor device as well as customizing the application on the user's mobile device.

As stated above, one type of customization that can be made to the firmware is configuring the sampling rate of one or more sensors to provide optimized data given a particular activity the user will perform. For example, a preinstalled version of the firmware can cause an accelerometer to generate accelerometer readings at a first sampling rate. This first sampling rate may be optimal for many common uses of the wearable sensor device.

However, a particular user may desire to use the wearable sensor device to monitor a movement for which a different sampling rate would be more optimal. As an example, the preinstalled version of the firmware may be optimized for exercises such as jogging, biking, or swimming where the speed of movement of the user's arm or leg is relatively slow. In contrast, the particular user may desire to use the wearable sensor device to monitor a golf swing or to track sprinting where the user's arm or leg is likely moving at a much higher speed.

In such cases, either by receiving user input identifying the intended use of the wearable sensor device or by detecting the actual use of the wearable sensor device while performing the desired movement, the mobile device can determine that a higher sampling rate would produce better accelerometer data for monitoring the golf swing or the sprinting motion. Accordingly, a customized update to the firmware can be provided to optimize the performance of the accelerometer during the golf swing or sprinting motion.

Also, to emphasize how the firmware is customized for a particular user, it is noted that one user's golf swing may require a different sampling rate for optimal performance than another user's golf swing. In such cases, an initial customized version of the firmware may be provided to each user's wearable device that is customized to monitor a golf swing. Then, after detecting the accelerometer data generated during the user's golf swing (or in response to user input), the mobile device may further customize the firmware for the particular user's golf swing.

Similarly, if one user intends to use a wearable device only for a first activity while another user intends to use a wearable device for a first and a second activity, different customized versions can be generated for each device. For example, in the first case, the sampling rate can be customized to be optimal for the first activity. In contrast, in the second case, the sampling rate can be customized to provide the best possible performance over the first and second activities (e.g. when each activity has a different optimal sampling rate).

In some embodiments, the particular version of firmware that is provided to a wearable sensor device can be generated by selecting from among a number of customizations available. For example, depending on the type of sensor being controlled, there may be various settings for controlling the sensor with various options that can be set for each setting. Depending on the information about the particular user, one or more settings for a sensor can be configured with the appropriate option to provide customized firmware that is most optimal for the particular user.

Referring to the sampling rate example above, there may be a number of different values to which a sensor's sampling rate can be set. The appropriate sampling rate for a particular user can be selected and specified in the customized version of the firmware for that particular user. Similarly, any other settings for the sensor or another sensor can be selected from among the various available options and specified in the customized version of the firmware. In this way, logic can be used to select the appropriate values for each configurable setting of a sensor based on the information known about a particular user.

In some embodiments, a wearable sensor device can be configured to automatically detect that its firmware is not optimal for the manner in which a particular user is using the wearable sensor device. In such cases, the wearable sensor device can automatically update its firmware to provide more optimal performance. For example, a wearable sensor device can initially be configured to use a sampling rate of 100 Hz. During use, the wearable sensor device can determine that a sampling rate of 50 Hz is sufficient for the types of activities the particular user performs while wearing the wearable sensor device. In response, the wearable sensor device can automatically update its firmware so that a sampling rate of 50 Hz is used.

Similarly, in some embodiments where a wearable sensor device is capable of automatically detecting that its firmware is not optimal, the wearable sensor device can be configured to cause firmware updates on other wearable sensor devices. For example, when the bracelet sensor device updates its firmware to use a sampling rate of 50 Hz, it may also cause another wearable sensor device (e.g. a shoe clip sensor device) to be updated with customized firmware for sampling at the 50 Hz rate. In this way, the bracelet sensor device can automatically customize the firmware on itself as well on the other wearable sensor device based on observations of how a particular user is using the devices.

In some embodiments, one wearable sensor device can be used to update the firmware of another wearable sensor device with an update received from a mobile device. For example, a bracelet sensor device can be configured to receive firmware updates from a mobile device (e.g. a mobile phone). The firmware updates can pertain to the bracelet sensor device or to another sensor device such as a shoe clip sensor device. In such cases, the bracelet sensor device can be configured to route the firmware update to the shoe clip sensor device so that the firmware on the shoe clip sensor device can be customized for a particular user.

An example of where one wearable sensor device can be used to update the firmware of another wearable sensor device is when one device is more powerful or has more capabilities than another device. Referring to the example above, a bracelet sensor device may be configured with the ability to wirelessly receive firmware updates from a mobile device while the shoe clip sensor device may not. In such cases, the bracelet sensor device and shoe clip sensor device can be provided with physical contact points which allow a direct transfer of firmware updates from the bracelet sensor device to the shoe clip sensor device. In this way, many wearable sensor devices can be updated with customized firmware without requiring each device to have the circuitry to wirelessly receive such updates from the mobile. This can result in wearable sensor devices that are smaller and require less battery power.

Figure 5:
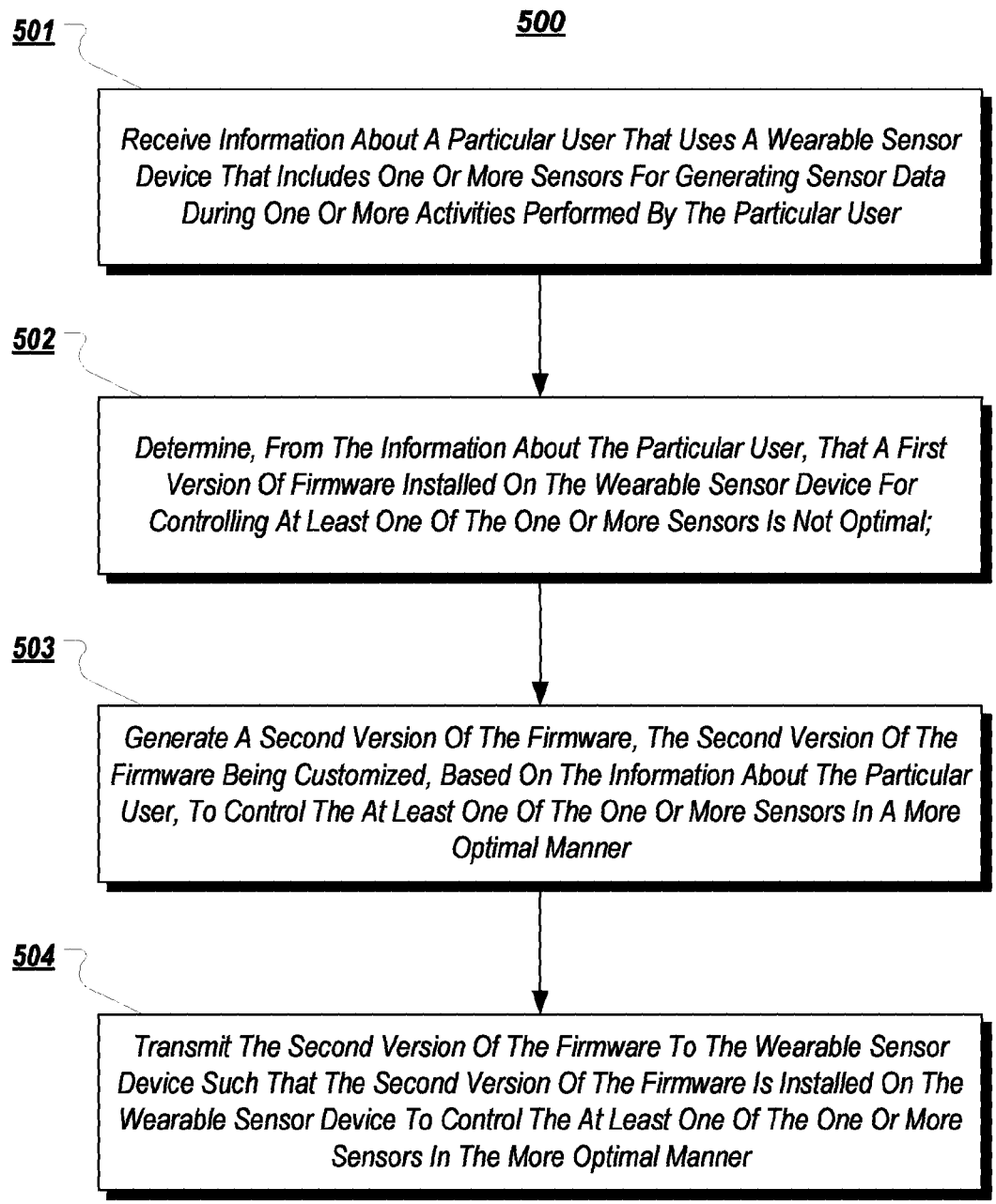
FIG. 5 illustrates a flowchart of an example method for providing a firmware update to a wearable sensor device.

FIG. 5 illustrates a flowchart of an example method 500 for providing a firmware update to a wearable sensor device where the firmware update is customized for a particular user that uses the wearable sensor device. Method 500 will be described with reference to FIGS. 3A-3C.

Method 500 includes an act 501 of receiving, by a mobile device, information about a particular user that uses a wearable sensor device that includes one or more sensors for generating sensor data during one or more activities performed by the particular user. For example, mobile device 301 can receive user information 320. User information 320 can identify various types of information about a particular user including the particular user's intended use of wearable sensor device 302, one or more characteristics of the particular user, one or more preferences of the particular user, etc.

Method 500 includes an act 502 of determining, from the information about the particular user, that a first version of firmware installed on the wearable sensor device for controlling at least one of the one or more sensors is not optimal. For example, mobile device 301 (or another computing device having access to user information 320 and knowing the current version of firmware on wearable sensor device 302) can determine that a customized firmware version should be installed on wearable sensor device 302 to cause one or more sensors of wearable sensor device 302 to perform in a customized manner.

Method 500 includes an act 503 of generating a second version of the firmware. The second version of the firmware is customized, based on the information about the particular user, to control the at least one of the one or more sensors in a more optimal manner. For example, second version of firmware 310b can be generated.

Method 500 includes an act 504 of transmitting, by the mobile device, the second version of the firmware to the wearable sensor device such that the second version of the firmware is installed on the wearable sensor device to control the at least one of the one or more sensors in the more optimal manner. For example, mobile device 301 can transmit (e.g. wirelessly via Bluetooth) the second version of firmware 310b to wearable sensor device 302 for installation such that sensor 303 is controlled in a manner customized and optimized for the particular user.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed:

1. A method for providing a firmware update to a wearable sensor device, the firmware update being customized for a particular user that uses the wearable sensor device, the method comprising:
   receiving, by a computing device, sensor data from a wearable sensor device that includes pulse oximeter, the sensor data being generated by the pulse oximeter while a particular user performs one or more activities while wearing the wearable sensor device such that the sensor data defines the particular user's blood oxygen level while the particular user performs the one or more activities, the sensor data being generated in accordance with a first version of firmware installed on the wearable sensor device;
   analyzing the sensor data to determine that the first version of the firmware is causing the pulse oximeter to generate sensor data that is not optimal for the particular user;
   generating a second version of the firmware, the second version of the firmware being customized, based on the analysis of the sensor data, to cause the pulse oximeter to generate sensor data in a more optimal manner for the particular user;
   transmitting, by the computing device, the second version of the firmware to the wearable sensor device such that the second version of the firmware is installed on the wearable sensor device to cause the pulse oximeter to generate sensor data in the more optimal manner; and
   wherein the customization in the second version of the firmware modifies:
     a power level at which a drive a component of pulse oximeter;
     a sampling rate at which the pulse oximeter generates sensor data; and
     a frequency at which generated sensor data is transmitted to the computing device.

2. The method of claim 1, wherein the wearable sensor device also includes one or more accelerometers that produce sensor data identifying the particular user's movements while performing the one or more activities, the method further comprising:
   analyzing the sensor data identifying the particular user's movements to identify the one or more activities that the particular user was performing while the sensor data was generated.

3. The method of claim 1, wherein determining that the first version of the firmware is causing the pulse oximeter to generate sensor data that is not optimal for the particular user comprises determining that power level of the pulse oximeter is not optimal for the particular user's skin; and
wherein the second version of the firmware is customized to modify the power level of the pulse oximeter to the optimal for the particular user's skin.

4. The method of claim 2, wherein the second version of the firmware is customized to cause the at least one of the pulse oximeter or the one or more accelerometers to employ a different sampling rate.

5. The method of claim 4, wherein the different sampling rate is optimal for at least one of the one or more activities.

6. The method of claim 1, wherein the second version of the firmware customizes one or more of:
   a sampling rate of the pulse oximeter;
   a power level supplied to one or more components of the pulse oximeter;
   whether sensor data from the pulse oximeter is stored in memory prior to being transmitted to the computing device; or
   whether a radio of the wearable sensor device is powered on during use of the wearable sensor device.

7. The method of claim 2, further comprising:
   processing the sensor data identifying the particular user's movements to identify the one or more activities that the particular user was performing while the sensor data was generated; and
   determining that a sampling rate of the one or more accelerometers is not optimal for the one or more identified activities; and
   wherein the second version of the firmware modifies the sampling rate of the one or more accelerometers to be optimal for the one or more identified activities.

8. The method of claim 1, further comprising:
   receiving input from the particular user that identifies one or more characteristics of the particular use; and
   wherein the second version of the firmware is also customized based on the input to cause the pulse oximeter to perform more optimally for the particular user having the one or more characteristic.

9. The method of claim 2, wherein the second version of the firmware is customized to cause the at least one of the pulse oximeter or the one or more accelerometers to provide optimal sensor data when the one or more performed activities are again performed.

10. The method of claim 9, wherein the second version of the firmware causes the at least one of the pulse oximeter or the one or more accelerometers to use a different sampling rate.

11. The method of claim 1, wherein the computing device generates the second version of the firmware.

12. The method of claim 1, further comprising:
   the wearable sensor device causing firmware on another wearable sensor device to be customized for a particular use of the other wearable sensor device.

13. The method of claim 12, wherein the wearable sensor device causing firmware on another wearable sensor device to be customized for a particular use of the other wearable sensor device comprises one or more of:
   transmitting, via a wired or wireless connection, customized firmware to the other wearable sensor device, wherein the customized firmware is either received from the computing device or generated by the wearable sensor device; or
   transmitting, via a wired or wireless connection, an instruction to the other wearable sensor device that causes the other wearable sensor device to customize its firmware.

14. A method for providing a firmware update to a wearable sensor device, the firmware update being customized for a particular user that uses the wearable sensor device, the method comprising:

receiving, by a computing device, information that identifies one or more exercises that particular user intends to perform while wearing the wearable sensor device, the wearable sensor device including one or more accelerometers for generating sensor data during the performance of the one or more exercises;

determining, from the information, that a first version of firmware installed on the wearable sensor device for controlling at least one of the one or more accelerometers will cause the at least one of one or more accelerometers to employ a sampling rate that is optimized for one or more other exercise but is not optimized for the one or more exercises that the particular user intends to perform;

generating a second version of the firmware, the second version of the firmware being configured to control the at least one of the one or more accelerometers to employ a sampling rate that is optimized for the one or more exercises that the particular user intends to perform;

transmitting, by the computing device, the second version of the firmware to the wearable sensor device such that the second version of the firmware is installed on the wearable sensor device to control the at least one of one or more activities that the particular user intends to perform; and wherein the customization in the second version of the firmware modifies:

a power level at which a drive a component of pulse oximeter;

a sampling rate at which the pulse oximeter generates sensor data; and a frequency at which generated sensor data is transmitted to the computing device.

15. The method of claim 14, wherein the wearable sensor device also includes a pulse oximeter and wherein the second version of the firmware also modifies a power level at which a drive a component of the pulse oximeter, the power level being optimized for the one or more exercises that the particular user intends to perform.

16. The method of claim 14, wherein the second version of the firmware is transmitted wirelessly to the wearable sensor device.

17. A method for providing a firmware update to a wearable sensor device, the firmware updating being customized for a particular user that uses the wearable sensor device, the method comprising:

receiving, by a mobile computing device, information that identifies one or more activities that a particular user intends to perform while wearing the wearable sensor device, the wearable sensor device including a pulse oximeter and one or more accelerometers for generating sensor data;

determining, from the information, that a first version of firmware installed on the wearable sensor device for controlling the pulse oximeter and the one or more accelerometers causes the pulse oximeter to employ a first power level and the one or more accelerometers to employ a first sampling rate that is are optimal for one or more other activities but not optimal for the one or more activities that the particular user intends to perform;

generating a second version of the firmware that is customized to cause the pulse oximeter to employ a second power level and the one or more accelerometers to employ a second sampling rate that are optimal for the one or more activities that the particular user intends to perform while wearing the wearable sensor device; and transmitting, by the mobile computing device, the second version of the firmware to the wearable sensor device such that the second version of the firmware is installed on the wearable sensor device to control the pulse oximeter to employ the second power level and the one or more accelerometers to employ second sampling rate; and wherein the customization in the second version of the firmware modifies:

a power level at which a drive a component of pulse oximeter;

a sampling rate at which the pulse oximeter generates sensor data; and a frequency at which generated sensor data is transmitted to the computing device.

* * * * *